(12) United States Patent
Frey et al.

(10) Patent No.: US 11,648,032 B2
(45) Date of Patent: May 16, 2023

(54) IMPLANT NEEDLE

(71) Applicant: Roche Diabetes Care, Inc., Indianapolis, IN (US)

(72) Inventors: Stephan-Michael Frey, Pfungstadt (DE); Oliver Kube, Worms (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 699 days.

(21) Appl. No.: 16/493,378

(22) PCT Filed: Mar. 12, 2018

(86) PCT No.: PCT/EP2018/056059
§ 371 (c)(1),
(2) Date: Sep. 12, 2019

(87) PCT Pub. No.: WO2018/166963
PCT Pub. Date: Sep. 20, 2018

(65) Prior Publication Data
US 2020/0008838 A1 Jan. 9, 2020

(30) Foreign Application Priority Data
Mar. 14, 2017 (EP) .................................... 17160727

(51) Int. Cl.
*A61B 17/34* (2006.01)
*A61M 5/32* (2006.01)
(Continued)

(52) U.S. Cl.
CPC ....... *A61B 17/3468* (2013.01); *A61M 5/3286* (2013.01); *A61B 5/14532* (2013.01);
(Continued)

(58) Field of Classification Search
CPC ........ A61B 17/3468; A61B 2017/3454; A61B 2017/320044; A61B 2560/063; A61M 37/0069; A61M 5/3286
See application file for complete search history.

(56) References Cited

U.S. PATENT DOCUMENTS 3,448,740 A   6/1969  Figge
5,752,942 A * 5/1998  Doyle .................... B24B 19/16
                                              604/274
(Continued)

FOREIGN PATENT DOCUMENTS

CN   1767871      5/2006
DE   42 35 483    4/1994
(Continued)

*Primary Examiner* — Thomas Mcevoy
(74) *Attorney, Agent, or Firm* — Woodard, Emhardt, Henry, Reeves & Wagner, LLP

(57) ABSTRACT

The present disclosure refers to an implant needle (1) for introducing an implant into a body of a patient, comprising a receiving portion configured to receive an implant and provided in a hollow needle main body (2), and a taper-shaped tip portion (3). The taper-shaped tip portion (3) is further comprising: a first slant surface (14a) contiguous to a first outer peripheral surface (15) of the hollow needle main body (2), wherein the first slant surface (14a) is provided as a first non-cutting edge; a second slant surface (16a) contiguous to a second outer peripheral surface (17) of the hollow needle main body (2), wherein the second slant surface (16a) is provided as a second non-cutting edge; and a pair of sharpened surfaces (9a, 9b) symmetric with respect to an edge point (10) and a longitudinal axis (13) of the needle main body (2), wherein the sharpened surfaces (9a, 9b) are both provided with a cutting edge. The first slant surface (14a) comprises a first flank (14b), and the second slant surface (16a) comprises a second flank (16b), wherein the first flank (14b) is provided at a first distance from the
(Continued)

Figure 1:
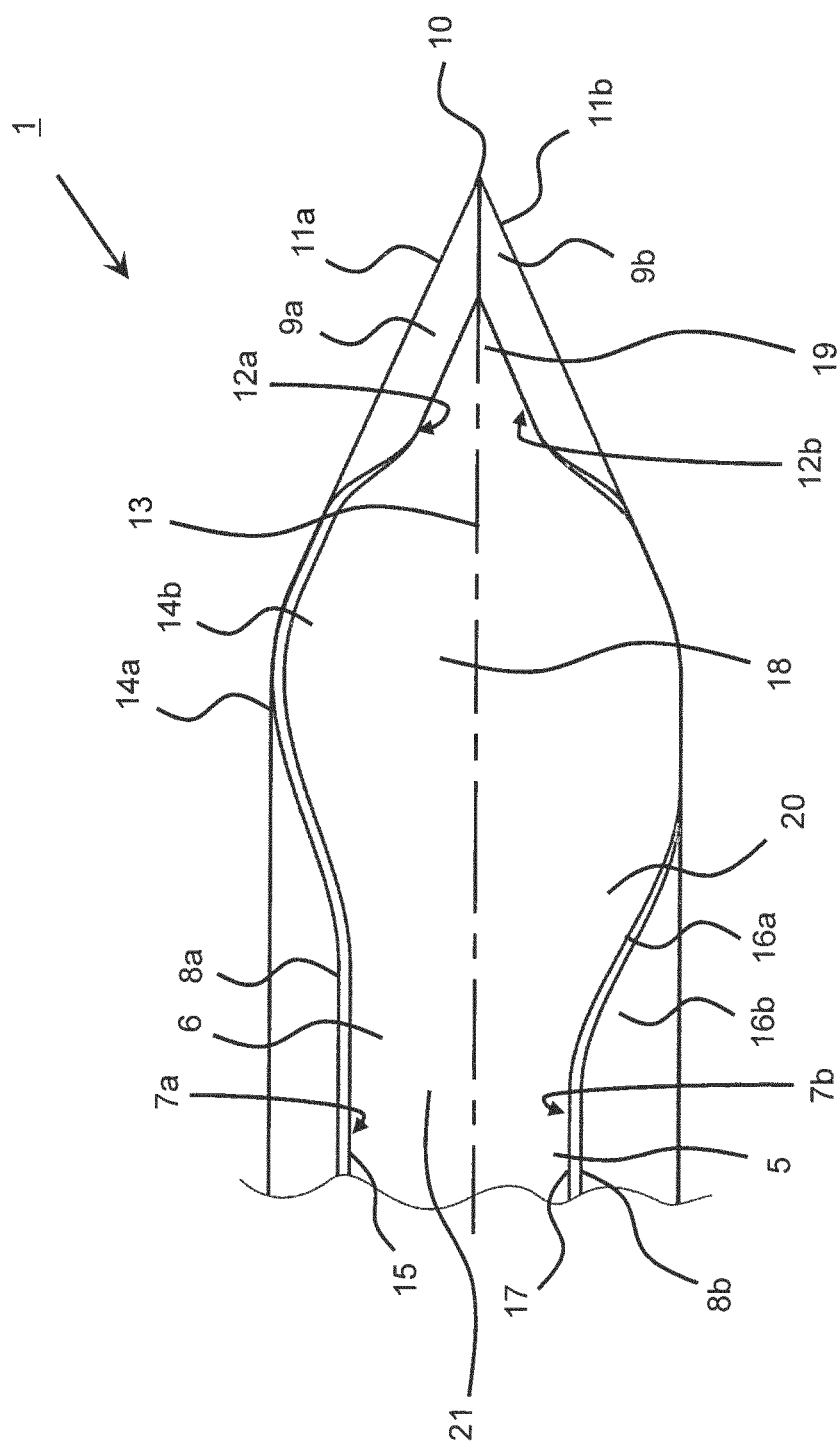

edge point (10) and the second flank (16*b*) is provided at a second distance from the edge point (10) which is different from the first distance.

19 Claims, 6 Drawing Sheets

(51) Int. Cl.
*A61B 5/145* (2006.01)
*A61B 5/1486* (2006.01)
*A61B 17/00* (2006.01)
*A61B 17/32* (2006.01)

(52) U.S. Cl.
CPC . *A61B 5/14865* (2013.01); *A61B 2017/00526* (2013.01); *A61B 2017/320044* (2013.01); *A61B 2017/3454* (2013.01); *A61B 2560/063* (2013.01)

(56) References Cited

U.S. PATENT DOCUMENTS

| | | | |
|---|---|---|---|
| 5,820,609 A * | 10/1998 | Saito | A61M 5/3286 |
| | | | 604/272 |
| 2003/0013934 A1 | 1/2003 | Schmidt | |
| 2005/0251190 A1 | 11/2005 | McFarlane | |
| 2007/0249992 A1 | 10/2007 | Bardy | |
| 2010/0249696 A1 | 9/2010 | Bardy | |
| 2016/0361091 A1 | 12/2016 | Frey et al. | |
| 2017/0216536 A1 * | 8/2017 | Scott | A61M 5/158 |

FOREIGN PATENT DOCUMENTS

| | | |
|---|---|---|
| EP | 1 491 225 | 12/2004 |
| JP | S55151341 | 11/1980 |
| WO | WO 2015/128263 | 9/2015 |

* cited by examiner

| Cannula sample number | $F_{max}$ N | $dL(F_{max})$ mm | $F_{min}$ N | $dL(F_{min})$ mm |
|---|---|---|---|---|
| C2.1-1 | 2,76 | 5,3 | -2,18 | 5,1 |
| C2.1-2 | 2,59 | 4,1 | -2,04 | 5,4 |
| C2.1-4 | 2,47 | 4,2 | -2,14 | 5,2 |
| C2.1-3 | 2,66 | 2,6 | -2,06 | 5,1 |
| C2.1-5 | 2,58 | 4,1 | -2,11 | 5,3 |
| C2.1-6 | 2,55 | 5,6 | -2,18 | 5,3 |
| C2.1-7 | 2,56 | 4 | -2,1 | 5,3 |
| C2.1-8 | 2,65 | 5 | -2,17 | 5,1 |
| C2.1-9 | 2,78 | 5,1 | -2,1 | 4,5 |
| C2.1-10 | 2,64 | 4,1 | -2,08 | 4,9 |
| C2.1-11 | 2,77 | 4,1 | -2,22 | 5,2 |
| C2.1-12 | 2,65 | 4,1 | -2,15 | 5,4 |
| C2.1-13 | 2,62 | 4,1 | -2,03 | 4,7 |
| C2.1-14 | 2,54 | 4,1 | -2,1 | 5,3 |
| C2.1-15 | 2,54 | 4,2 | -2,17 | 5,4 |
| C2.1-16 | 2,7 | 2,5 | -2,14 | 5,3 |
| C2.1-17 | 2,64 | 4 | -2,05 | 5,1 |
| C2.1-18 | 2,64 | 4,2 | -2,11 | 5,4 |
| C2.1-19 | 2,64 | 4 | -2,14 | 5,1 |
| C2.1-20 | 2,64 | 4 | -2,12 | 5,4 |

Fig. 7

IMPLANT NEEDLE

The present disclosure relates to an implant needle for introducing an implant into a body of a patient.

BACKGROUND

For inserting implants, e.g. sensors, into the skin up to an insertion depth of approximately 10 mm different types of implant cannula or needles are known, e.g. closed cannulas with a V-bevel, oval-shaped slotted cannulas with a V-bevel, and peel catheters, i.e. a cannula tube divided into two with a V-bevel which is then opened in the skin and removed in separate parts.

A flat sensor cannot be inserted into the skin with closed implant needles with a V-bevel, tubular. Oval-shaped slotted implant cannulas or needles are more expensive to manufacture than tubular slotted cannulas. They are predominantly used for 90° insertion angles. Peel catheters are also more expensive to manufacture and usually are only allowed to be inserted and removed by a doctor or nurse.

Document WO 2015/128263 A1 discloses an implant needle for introducing an implant into a body of a patient is provided. The implant needle comprises a receiving portion configured to receive an implant and provided in a hollow needle main body, and a taper-shaped tip portion formed by cutting a tip portion of the hollow needle main body. The implant needle may also be referred to an implant cannula. The taper-shaped tip portion comprises a first slant surface provided contiguous to an outer peripheral surface of the hollow needle main body. The first slant surface is formed at a pre-determined angle with respect to an axis of the needle main body. The first slant surface may also be referred to as primary or base cut. The taper-shaped tip portion further comprises a pair of second slant surfaces contiguous to the first slant surface and symmetric with respect to an edge point and the axis of the hollow needle main body. The pair of second slant surfaces is formed at a larger angle with respect to the axis of the needle main body than the predetermined angle with respect to the axis of the needle main body. The pair of second slant surfaces may also be referred to as facet cut. An outer edge of the pair of second slant surfaces is provided as a cutting edge contiguous to the edge point. The inner and outer edges of the first slant surface are provided as non-cutting edges.

Document DE 10 2011 112 021 A1 discloses a needle or cannula prided with a tapered tip portion. Also, Document DE 102 24 101 A1 refers to cannula prided with a tapered tip portion. There are a first slant surface provided contiguous to an outer peripheral surface of the hollow needle main body and a pair of second slant surfaces contiguous to the first slant surface and symmetric with respect to an edge point and the axis of the hollow needle main body.

Document WO 99/53991 A1 refers to an implant retention trocar which includes a cannula for puncturing the skin of an animal and an obturator for delivering the implant beneath the skin of the animal. The implant retention trocar has a cannula distal tip design which causes a minimum of trauma and tearing of tissue during implant insertion. A spring element received within the cannula prevents an implant which is to be inserted into an animal from falling out of the cannula during the implant insertion process. The spring element includes a longitudinal leg which is folded with a zig-zag shaped bend. When the spring element is inserted into the cannula the zig-zag shaped bend of the shaped bend of the longitudinal leg retains the implant within the cannula.

Document US 2010/324579 discloses an instrument with a covered bore for subcutaneous implantation. An incising body defines a non-circular coaxial bore and includes a sharpened cutting edge that extends from a bottom distal end beyond the opening of the coaxial bore and an attachment point at a top distal end. A plunger is non-fixedly contained within the coaxial bore and slides longitudinally therein. A cover is pivotally attached at the attachment point and extends down to the bottom distal end and, when closed, the cover encloses the opening proximal to the cutting edge.

Document U.S. Pat. No. 3,064,651 relates to a hypodermic needle comprising an axial bore and being beveled at its outer end to provide a tissue penetrating tip and an obliquely disposed bore orifice extending rearwardly from said tip.

Document U.S. Pat. No. 3,448,740 refers to a non-coring hypodermic needle, comprising a heel portion and a tip portion terminating in a piercing point characterized in that at least one side wall portion is spirally curved from the piercing point to the heel portion and the heel portion is rotatably displaced approximately within the range of 260° to 280° and preferably about 270° from the piercing point in the same direction as the direction of spiral of said side wall portion.

Document WO 2005/044116 discloses a cutting device for a blunt needle or transcutaneous sensor for insertion through the derma of a patent, said blunt needle or transcutaneous sensor having a circumference at the distal end, said cutting device comprising a base part and a cutting member for making an incision in the derma, said base part having a track adapted for slideable engagement with the needle or transcutaneous sensor, wherein the cutting member has a cutting width, W, being less than half the length of the circumference of the blunt needle or transcutaneous sensor.

Document U.S. Pat. No. 4,490,139 refers to a subcutaneous implant needle formed as a hollow tube having its forward end cut on a plane at an acute angle to the central axis of the tube to form an elliptical opening, and an elliptical outer edge having a sharp forward portion. The forward extremity of the needle is dressed to form cutting edges intersecting at an obtuse angle and forming a central point. The dressed edges have a width preferably less than two-thirds the diameter of the tube, and the adjoining side portions of the elliptical outer edge are rendered non-sharp and dulled, as by abrasion such as sandblasting or tumbling in abrasive media. The needle is dimpled at two locations closely adjacent the rear of the opening.

Document EP 1 491 225 A1 discloses an injection needle comprising a needle tip provided by forming at least two or more ground surfaces after a first ground surface is formed at the tip of a needle tube, characterized in that the needle tip is not present on a central plane, where a plane vertically crossing the first ground surface and including the center axis of the needle tube is the central plane, whereby the injection needle can reduce boring pain provided to a patient when the needle is pierced into a skin.

Document DE 42 35 483 A1 refers to a hollow cannula for injection or liquid withdrawal that has circular shaft cross-section and an inclined ellipsoidal piercing face with two side cutting edges which meet at the cannula tip. The cannula is asymmetrical in the region of the cutting edges. The cutting edges may have unequal lengths and/or form unequal angles with the cannula axis.

Document US 2005/251190 A1 relates to a tissue penetrating instrument of the type used in the medical field and which may or may not be embodied in the form of an obturator associated with a trocar assembly, wherein the instrument includes an elongated shaft having a penetrating tip mounted on one end thereof. The penetrating tip includes a base secured to the one end of the shaft, and a distal extremity spaced longitudinally outward from the base and formed into an apex which may be defined by a point or other configuration specifically structured to facilitate penetration or puncturing of bodily tissue. The apex may be substantially aligned with a linear extension of the central longitudinal axis of the shaft or alternatively, may be spaced laterally outward or offset from the central longitudinal axis of the shaft. The penetrating tip further includes an exterior surface extending continuously between the apex and the base and configured to facilitate puncturing of the tissue and an enlargement of an access opening formed in the tissue, in a manner which facilitates separation of the tissue and minimizes cutting, severing or otherwise damaging the contiguous bodily tissue surrounding the access opening.

SUMMARY

It is an object to provide an improved implant needle for introducing an implant, for example a sensor device such as an analyte sensor, preferably an electrochemical sensor such as a glucose sensor, into a body of a patient. The implant needle shall allow for non-destructive implantation of the implant.

The implant needle may be configured for implanting an implant transcutaneous where a part of the implant is placed under the skin and another part of the implant is above the skin. In an alternative, the implant needle may be configured for a full implantation where the entire implant is placed under the skin. Further, the implant needle shall support conservative implantation into the patient's body.

According to the present disclosure, an implant needle for introducing an implant into a body of a patient according to claim 1 is provided. Alternative embodiments are disclosed in the dependent claims.

According to an aspect, an implant needle for introducing an implant into a body of a patient is provided. The implant needle comprises a receiving portion configured to receive an implant and provided in a hollow needle main body, and a taper-shaped tip portion. The taper-shaped tip portion is further comprising: a first slant surface contiguous to a first outer peripheral surface of the hollow needle main body, wherein the first slant surface is provided as a first non-cutting edge; a second slant surface contiguous to a second outer peripheral surface of the hollow needle main body, wherein the second slant surface is provided as a second non-cutting edge; and a pair of sharpened surfaces symmetric with respect to an edge point and an longitudinal axis of the needle main body, wherein the sharpened surfaces are both provided with a cutting edge. The first slant surface comprises a first flank, and the second slant surface comprises a second flank. The first flank is provided at a first distance from the edge point, and the second flank is provided at a second distance from the edge point which is different from the first distance.

A hollow needle main body of an implant needle in the sense of the application is a hollow body that is provided with an opening extending in a longitudinal direction of the implant needle in a side of the hollow needle main body. Thus, the hollow needle main body may also be referred to as an open hollow needle main body. In other words, the hollow needle main body is not a cannula provided with a closed tube shape.

The opening in the side of the hollow needle main body may extend along the entire length of the hollow needle main body. Alternatively, the opening in the side of the hollow needle main body may only extend along part of the length of the hollow needle main body. In case the opening extends only along part of the length of the hollow needle main body, the opening extends to a distal end of the hollow needle main body, providing an opening towards the taper-shaped tip portion.

The opening in the side of the hollow needle main body may be formed symmetric with respect to the longitudinal axis of the needle main body. The opening in the side of the hollow needle main body may be provided as a slot opening. Thereby, a slotted hollow needle main body may be provided.

The opening in the side of the hollow needle main body may enable a contacting end of an implant to be placed in a position outside the receiving portion of the hollow needle main body.

The opening in the side of the hollow needle main body may enable retracting the implant needle from the body of the patient when the implant has been inserted without changing the position of the implant.

Inner edges formed in the range of the opening in the side of the hollow needle main body may be provided as non-cutting edges.

The tapered tip portion, for example, may be formed by cutting a tip portion of the hollow needle main body.

The sharpened surfaces both may be provided as a non-slanted surface in a flat tip portion contiguous to the edge point. The flat tip portion may be symmetric to the longitudinal axis of the needle main body.

At least one of the first and second flanks may be contiguous to one of the sharpened surfaces.

At least one of the first and second flanks may be contiguous to the cutting edge provided to the one of the sharpened surfaces.

At least another one of the first and second flanks may be contiguous to a non-sharpened surface which in turn is contiguous to the sharpened surface having the cutting edge. The non-sharpened surfaces are free of any cutting edge, thereby, being provided with non-cutting edges. The non-sharpened surface may be provided in the flat tip portion.

For at least one of the first and second flanks, the first and second outer peripheral surface may be bent outwardly.

For at least one of the sharpened surfaces the cutting edge may be provided on an outer edge. An inner edge may be provided with a non-cutting edge. In an alternative embodiment, the inner edge may be provided with a cutting edge, while the outer edge is provided with a non-cutting edge. In still a further alternative embodiment, both the outer edge and the inner edge of the sharpened surfaces may be provided with a cutting edge.

The first and second flank both may be provided as a punch-bent component.

At least one of the first and second flanks may be provided adjacent to a flat portion distal to the edge point.

The flat portion may be contiguous to the flat tip portion.

The receiving portion may comprise a recess extending through the needle main body. The recess may be formed symmetric with respect to the longitudinal axis of the needle main body.

The hollow needle main body may be provided with one of a round cross-section and an oval cross-section.

The tapered tip portion may be provided with a flat portion.

In the sense of the application, a cutting edge will cut the skin while a non-cutting edge will not usually cut the skin. For example, a cutting edge may be obtained by thinning of material towards the edge.

Non-cutting edges, for example, can be produced by grinding or laser cutting or water cutting. Non-cutting edges may be produced by rounding edges after cutting the material.

One or more of the non-cutting edges may be provided as rounded edges. Finishing through blasting with materials or polishing may be used for rounding the edge. Blasting can be carried out with, for example, glass spheres, corundum, and sand. A well-known method is polishing, for example electropolishing in fluid.

In the process of production, rounding may be provided by grinding and/or electropolishing. In addition or as an alternative, abrasive material blasting may be used. Alternatively, the non-cutting edges may be produced by applying abrasive material blasting only.

The hollow needle body may be provided with a U- or V-shaped cross section in the receiving portion. With respect to the taper-shaped tip portion, a bevel may be provided. The opening in the side of the hollow needle main body may be contiguous to the bevel provided with respect to the taper-shaped tip portion.

In the following it is described how the implant needle can be manufactured. The method may comprise a) punching a flat metal strip or sheet so as to give rise to a flat sheet of a desired shape suitable for later bending the sheet so as to give rise to the shape of the cannula or implant needle. In a second step b) the sheet may then be subjected to embossing of the "dull" non-cutting edges in the portion of the sheet. Then, in a step c) the cannula may be bent and the tip of the cannula may be embossed and punched out so as to give rise to the cannula of the invention. As an alternative, etching methods can be used to create a sharp tip of the cannula.

The method for manufacturing the implant needle may comprise producing at least the first and second flanks by at least one of a punch-bent process or an etching process combined with a bent process. The punch-bent process combining punching and bending the material used for manufacturing the implant needle are combined for producing at least one of the flanks. Such punch-bent process may be used for manufacturing the hollow needle main body as well.

The method may comprise: Providing a hollow needle main body having a lumen surrounded by a peripheral wall and a receiving portion configured to receive an implant and provided in the hollow needle main body. The taper-shaped tip portion is produced with a first slant surface contiguous to a first outer peripheral surface of the hollow needle main body, wherein the first slant surface is provided as a first non-cutting edge; a second slant surface contiguous to a second outer peripheral surface of the hollow needle main body, wherein the second slant surface is provided as a second non-cutting edge; and a pair of sharpened surfaces symmetric with respect to an edge point and an longitudinal axis of the needle main body, wherein the sharpened surfaces both are provided with a cutting edge. The first slant surface comprises a first flank and the second slant surface comprises a second flank. The first flank is provided at a first distance from the edge point and the second flank is provided at a second distance from the edge point which is different from the first distance.

DESCRIPTION OF FURTHER EMBODIMENTS

Figure 2:
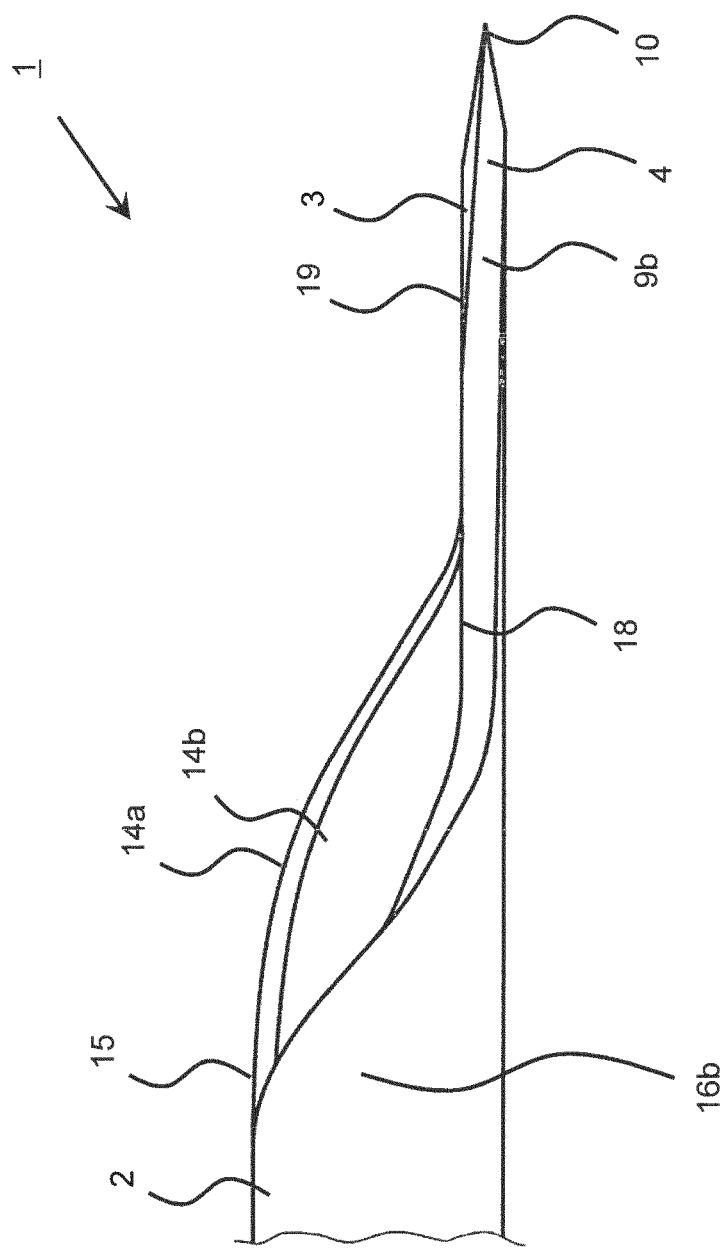
Figure 4:
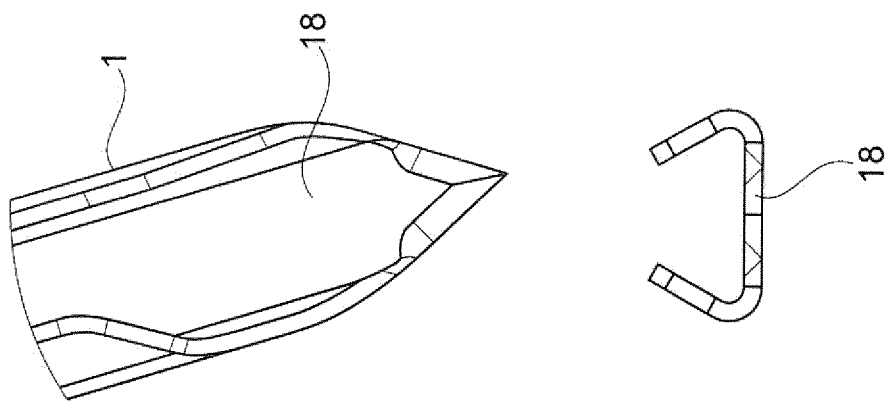
Figure 3:
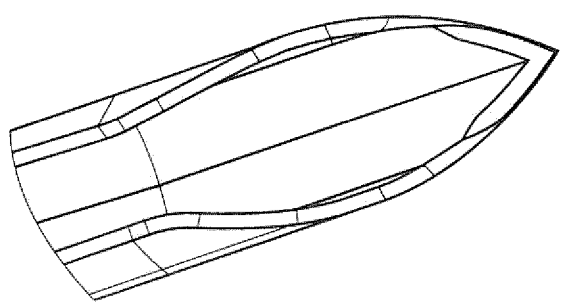
Figure 5:
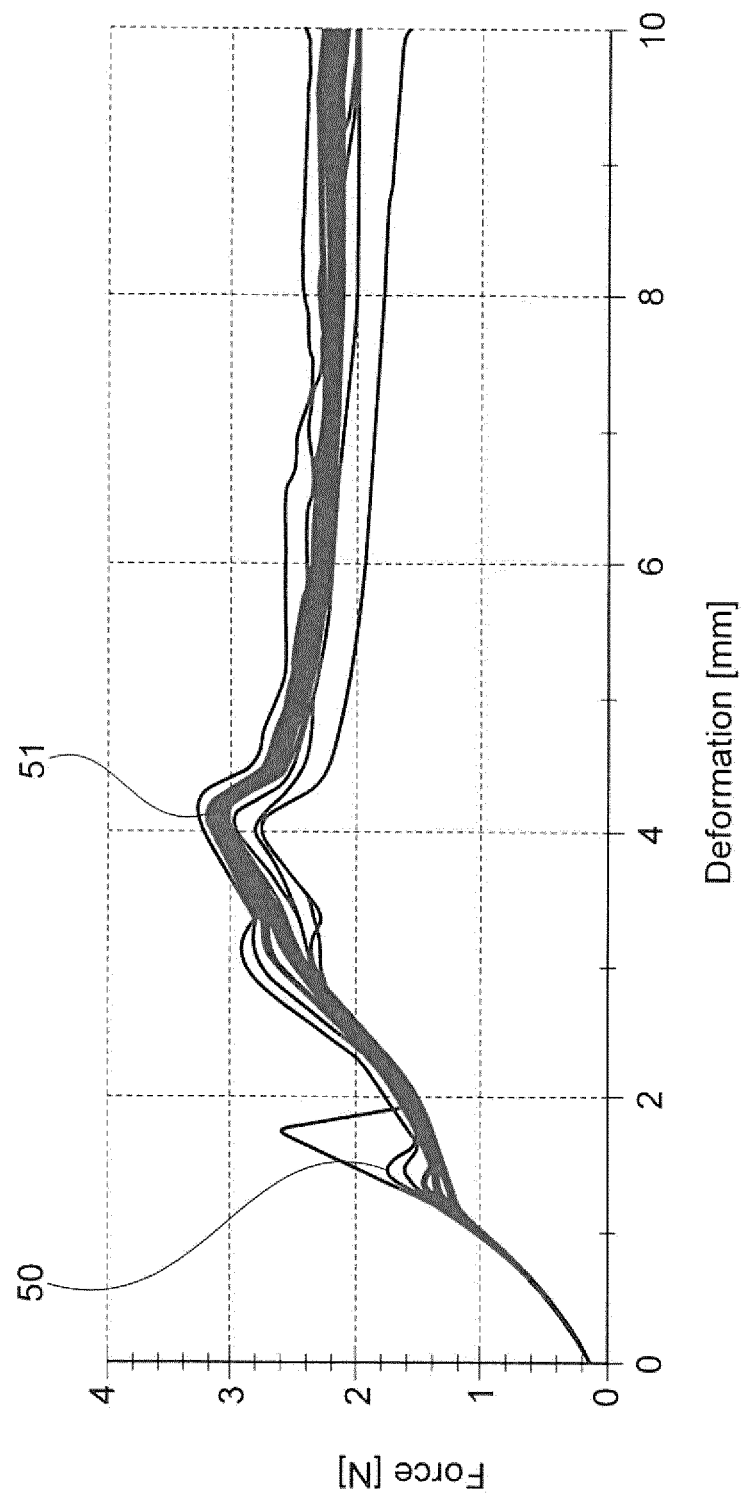
Figure 6:
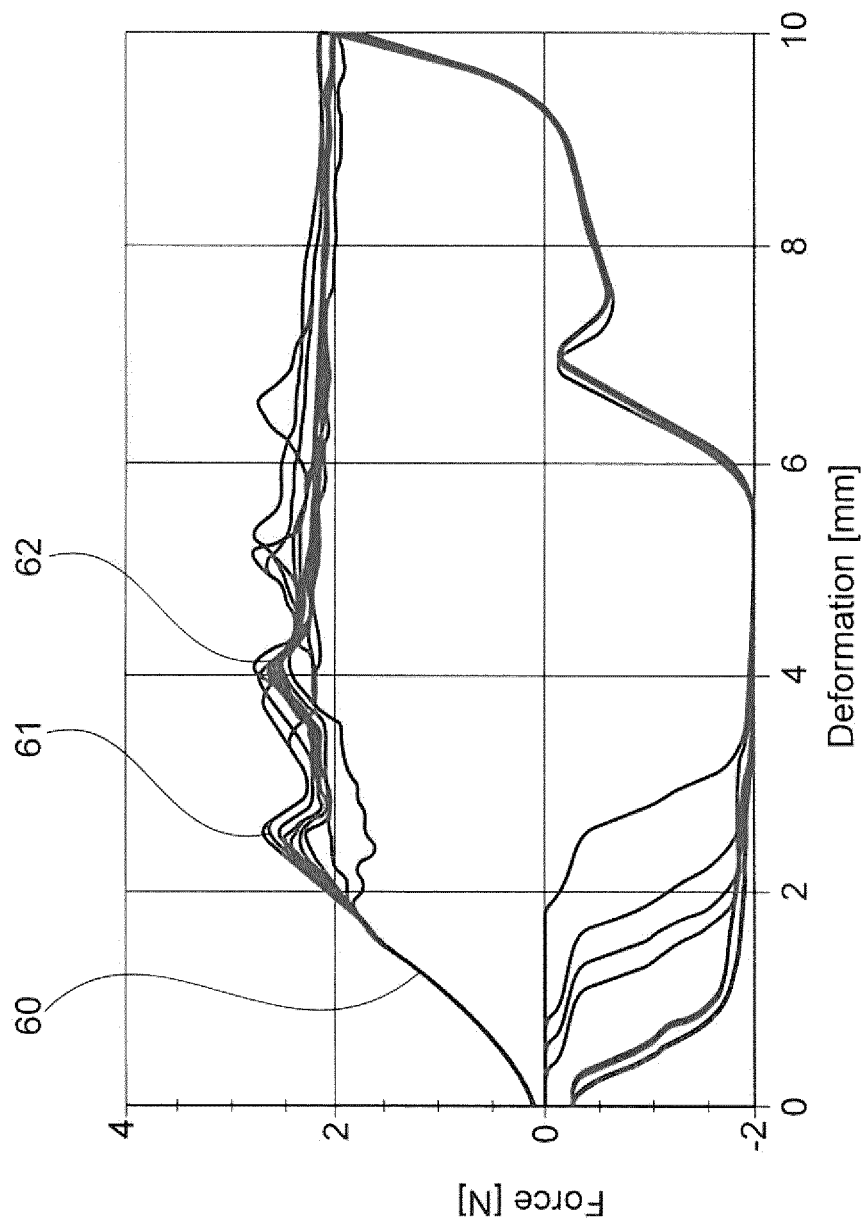

In the following, further embodiments will be described by way of example. In the figures show:

FIG. 1 a top view of a tip section of an implant needle having a hollow needle or cannula main body provided with a taper-shaped tip portion;

FIG. 2 a side view of the tip section in FIG. 1;

FIG. 3 an implant needle with symmetrical flank known in the art;

FIG. 4 a implant needle, wherein a first flank is provided at a first distance from an edge point, and a second flank is provided at a second distance from the edge point which is different from the first distance;

FIG. 5 a graphical representation of the penetration force the implant needle shown in FIG. 3;

FIG. 6 a graphical representation of the penetration forces of the implant needle shown in FIG. 4; and FIG. 7 experimental results for the implant needle in FIG. 4.

Referring to FIGS. 1 and 2, an implant needle 1 having a hollow needle or cannula main body 2 is provided. The hollow needle main body 2 is provided with a taper-shaped tip portion 3 at an end 4.

The hollow needle main body 2 comprises a receiving section 5 provided with an opening extending in a longitudinal direction of the implant needle which, in the embodiment shown, is in the form of a slot opening 6. The slot opening 6 may extend along the entire length of the hollow needle main body 2 (not shown in its entire length in FIGS. 1 and 2) or along a section of the hollow needle main body 2.

The receiving section 5 is configured to receive an implant element (not shown), e.g. a sensor, to be introduced into the body of a human being or an animal through the skin by the implant needle 1. For implantation the implant is located in the receiving section 5. After puncturing through the skin into the body, the implant needle 1 is retracted leaving the implant in the body. The implant element slides out of the receiving section 5 when the implant needle 1 is retracted.

Inner edges 7a, 7b formed in the range of the slot opening 6 or the receiving section 5 are provided as non-cutting edges. This will also support preventing the implant element from damage when the implant element is leaving the receiving section 5 during implantation. Also, outer edges 8a, 8b are provided as non-cutting edges.

In the taper-shaped tip portion 3, a pair of sharpened surfaces 9a, 9b is provided. The pair of sharpened surfaces 9a, 9b is formed contiguous to an edge point 10. Outer edges 11a, 11b of the sharpened surfaces 9a, 9b are provided as cutting edges. Inner edges 12a, 12b of the sharpened surfaces 9a, 9b, according to the embodiment shown, are provided as non-cutting edges.

The sharpened surfaces 9a, 9b are symmetric to the edge point 10 and a longitudinal axis 12 of the needle main body 2.

A first slant surface 14a is provided on a first flank 14b contiguous to a first outer peripheral surface 15 of the hollow needle main body 2. A second slant surface 16a is provided on a second flank 16b contiguous to a second outer peripheral surface 17 of the hollow needle main body 2. The first flank 14b is provided at a first distance from the edge point 10. The second flank 15b is provided at a second distance from the edge point 10, wherein the first distance is different from the second distance, thereby, providing an asymmetric design of location for the first and second flank 14b, 16b with regard to the edge point 10.

The first flank 14b is provided adjacent to a flat portion 18 which in turn is contiguous to a flat tip portion 19. In the embodiment shown, the first flank 13b is provided in a center portion of the flat portion 18, while the second flank 16b also located adjacent to the flat portion 18 is provided in a distal end portion 20 of the flat portion 18, the distal end portion 18 being more distant to the edge point 10. The second flank 16b may be located in a transition portion in which a non-flat portion 21 of the hollow needle main body 2 is contiguous to the flat portion 18.

With regard to the first and the second flanks 14b, 16b, the first and second outer peripheral surfaces 15, 17 is bent outwardly. The extent to which the first and second outer peripheral surfaces 15, 17 are bent outwardly may be the same. In an alternative, the first and second outer peripheral surfaces 15, 17 may be bent outwardly to different extent.

If the implant needle 1 is used for cutting a skin the skin is cut by the sharpened surfaces 9a, 9b. Following, because of the non-cutting edges the skin is lifted by the first and the second flank 14b, 16b. Firstly, the skin is lifted by the first flank 14b on the one side of the implant needle 1. Later when the taper-shaped tip portion 3 is further introduced into the skin, the skin is lifted by the second flank 16b. Therefore, the lifting of the skin is done step by step which supports an undestructive implantation of the implant to be introduced in the patient's body by the implant needle 1.

In the process of manufacturing the implant needle 1 at least the first and second flanks 14b, 16b may be produced by at least one of a punch-bent process and an etching process combined with a bent process. The punch-bent process combining punching and bending the material used for manufacturing the implant needle 1 are combined for producing at least one of the first and second flanks 14b, 16b. Such punch-bent process may be used for manufacturing the hollow needle main body 2 as well.

The method for production may comprise punching a flat metal strip or sheet so as to give rise to a flat sheet of a desired shape suitable for later bending the sheet so as to give rise to the shape of the cannula. In a further step, the sheet may then be subjected to embossing of the "dull" noncutting edges in the portion of the sheet. Then, in another step, the cannula may be bent, and the tip portion of the cannula may be embossed and punched out so as to give rise to the cannula. As an alternative etching methods can be used to create a sharp tip of cannula.

The implant needle according to the alternative embodiments provides for the surprising advantage that the manufacturing of the implant needle which starts with a flat metal sheet allows for cheaper and faster production of the needle than the expensive manufacturing processes used to generate state of the art needles made by cutting and sharpening of cylindrical closed metal cylinders.

Different cannula or implant needle types were tested. FIG. 3 shows an implant needle having symmetrical flank and a cross section essentially round as known in the art. FIG. 4 shows an implant needle 1 as depicted in FIGS. 1 and 2.

FIGS. 5 and 6 each how a graphical representation of the penetration force measured for the implant needle shown in FIG. 3 and the implant needle shown in FIG. 4, respectively.

The implant needle from FIGS. 1, 2, and 4 are configured to support reduced penetration forces during insertion into skin when compared to the implantation needle with symmetrical edges such as the one depicted in FIG. 3. This surprising result in turn reduces the pain for the patient using such needles.

The implant needles from FIGS. 3 and 4 were tested by simulating insertion into human skin by a procedure according to German standard DIN 13097-4 as follows: A (PUR) film according DIN 13097-4 (polyurethane testing foil strips by melab Medizintechnik and Labor GmbH, Leonberg, Germany) was fixed in a test stand and used in place as a model system of skin. In each test, an individual piece of the PUR film was penetrated by the implant needle under investigation.

For each of the two implant needles, the following parameters as well as their respective mean values and standard deviations were determined: F0—Force [N] exerted by the needle tip penetrating the PUR film; Fmax—Maximal force [N] exerted by entry of the broadest part of the needle tip (represented by the respective tips flank or flanks) into the PUR film; and Fmin—Minimum force [N] exerted when the needle is retracted from the PUR film.

The experiment was performed according to standard DIN 13097-4 for penetration testing. The test procedure comprises the consecutive steps of clamping of the implant needle, starting the software routine, moving of the PUR film and unclamping of the implant needle.

FIG. 7 depicts experimental results for the implant needle in FIG. 4 referred to "C2.1-x" with x=1 . . . 20. The average value of maximal penetration forces Fmax detected for the tested implant needles is 2.63N.

The implant needle from FIG. 4 shows a lower maximal penetration force Fmax, and also the lowest standard deviation. The implant needle from FIG. 4 is associated with a superior performance under the conditions of the model skin which supports the view that comparable performance can be demonstrated under the "physiological" circumstances of an insertion into the skin of a user.

It is noteworthy that the implant needle from FIG. 3 having symmetrical flanks showed a low performance (see below). The needle cross section in the area of the tip led to an increased penetration force which should be associated with an increased pain for the patient when compared to the implant needle in FIG. 4.

Referring to FIG. 5, when penetrating the model skin with the implant needle from FIG. 3 both symmetrical flanks penetrated the film simultaneously and the widening of the skin model took place in one step. The maximum force was exerted when both flanks entered the skin model. In FIG. 5 there are two local maxima: 50—entry of the needle tip into the skin, and 51—entry of the needle flanks.

Table 1 shows experimental results for the implant needle in FIG. 3.

TABLE 1

| Series n = 50 | Fmax [N] |
| --- | --- |
| Minimum force | 2.77 |
| Maximum force | 3.31 |
| Mean value | 3.1 |
| Standard deviation | 0.11 |
| Range | 0.81 |

Referring to FIG. 6, when penetrating the model skin with the implant needle from FIG. 4 the flanks penetrated the film at different times, i.e. the flank provided as a shorter distance from the edge point penetrated the film before the flank provided as a larger distance from the edge point 10. The maximum force was exerted when both flanks entered the skin model. In FIG. 6 there are three local maxima: 60—entry of the needle tip into the skin, 61—entry of the first needle flanks, and 62—entry of the second needle flank. While the entry of the needle tip 60 is a rather small local maximum, the other maxima are well established on the plot shown in FIG. 6.

Table 2 shows experimental results for the implant needle in FIG. 4.

TABLE 2

| Series n = 20 | Fmax [N] | dL (Fmax) [mm] | Fmin [N] | dL (Fmin) [mm] |
|---|---|---|---|---|
| Minimum force | 2.47 | 2.5 | −2.2 | 4.5 |
| Maximum force | 2.78 | 0.7 | 0.0507 | 0.2 |
| Mean value | 2.63 | 4.2 | −2.12 | 5.2 |
| Standard deviation | 0.0797 | 5.6 | −2.03 | 5.4 |

The second maximum 61 in the plot "deformation path versus penetration force" in FIG. 6 was due to the fact that the first flank raised the PUR film and widened the puncture site further without cutting. Then the force dropped slightly, since only the sliding friction prevailed. The third maximum 62 was due to the fact that the second flank raised the PUR film and finally expanded the puncture site to the implant needle cross-section. After that there was only sliding friction.

The asymmetry of the cannula flanks along the longitudinal axis resulted in a reduction of the incision force of about 3N to about 2.6N compared to the prior art needle, which was due to the fact that the expansion of the PUR film at the puncture site took place gently and step by step by one flank after the other and on a longer puncture path.

The sliding friction of the implant needle from FIG. 4 was still unchanged at the same level between 2N and 2.1N.

Based on the above results, implant needle from FIG. 4 provides for significantly reducing maximum penetration forces of the PUR film compared to the known implant needle.

The invention claimed is:

1. An implant needle for introducing an implant into a body of a patient, comprising
    a receiving portion configured to receive an implant and provided in a hollow needle main body, and
    a taper-shaped tip portion, the taper-shaped tip portion further comprising:
        a first slant surface contiguous to a first outer peripheral surface of the hollow needle main body, wherein the first slant surface is provided as a first non-cutting edge;
        a second slant surface contiguous to a second outer peripheral surface of the hollow needle main body, wherein the second slant surface is provided as a second non-cutting edge; and
        a pair of sharpened surfaces symmetric with respect to an edge point and a longitudinal axis of the needle main body, wherein the sharpened surfaces are both provided with a cutting edge,
    the taper-shaped tip portion being tapered down in the direction of the edge point, and the first and second slant surfaces being slanted down relative to the longitudinal axis in the direction of the edge point;
    wherein the first slant surface comprises a first flank and the second slant surface comprises a second flank, and wherein the first slant surface is provided starting at a first distance from the edge point and extending away from the edge point, and the second slant surface is provided starting at a second distance from the edge point and extending away from the edge point, the second distance being different from the first distance.

2. The implant needle according to claim 1, wherein the sharpened surfaces both are provided as a non-slanted surface in a flat tip portion contiguous to the edge point.

3. The implant needle of claim 2 in which the flat tip portion extends in a plane that is parallel to the longitudinal axis of the implant needle.

4. The implant needle according to claim 1, wherein at least one of the first and second flanks is contiguous to one of the sharpened surfaces.

5. The implant needle according to claim 4, wherein the at least one flank is contiguous to the cutting edge of one of the sharpened surfaces.

6. The implant needle according to claim 5, wherein at least another one of the first and second flanks is contiguous to a non-sharpened surface which in turn is contiguous to the cutting edge of the other sharpened surface.

7. The implant needle according to claim 1, wherein, for at least one of the first and second flanks, the first and second outer peripheral surface is bent outwardly.

8. The implant needle according to claim 1, wherein, for at least one of the sharpened surfaces, the cutting edge is provided on an outer edge.

9. The implant needle according to claim 1, wherein the first and second flanks both are provided as a punch-bent component.

10. The implant needle according to claim 1, wherein at least one of the first and second flanks is provided adjacent to a flat portion distal to the edge point.

11. An implant needle for introducing an implant into a body of a patient, comprising:
    a receiving portion configured to receive an implant and provided in a hollow needle main body, and
    a taper-shaped tip portion, the taper-shaped tip portion further comprising:
        a first slant surface contiguous to a first outer peripheral surface of the hollow needle main body, wherein the first slant surface is provided as a first non-cutting edge;
        a second slant surface contiguous to a second outer peripheral surface of the hollow needle main body, wherein the second slant surface is provided as a second non-cutting edge; and
        a pair of sharpened surfaces symmetric with respect to an edge point and a longitudinal axis of the needle main body, wherein the sharpened surfaces are provided with a cutting edge and are provided as a surface in a flat tip portion contiguous to the edge point,
    the taper-shaped tip portion being tapered down in the direction of the edge point, and the first and second slant surfaces being slanted down relative to the longitudinal axis in the direction of the edge point;
    wherein the first slant surface comprises a first flank and the second slant surface comprises a second flank, and wherein the first slant surface is provided starting at a first distance from the edge point and extending away from the edge point, and the second slant surface is provided starting at a second distance from the edge point and extending away from the edge point, the second distance being different from the first distance, and
    wherein a flat portion is contiguous to the flat tip portion.

12. The implant needle according to claim 1, wherein the receiving portion comprises a recess extending through the needle main body.

13. The implant needle according to claim 1, wherein the hollow needle main body is provided with one of a round cross-section and an oval cross-section.

14. The implant needle according to claim 1, wherein the tapered tip portion is provided with a flat portion.

15. The implant needle according to claim 1, wherein one or more of the non-cutting edges are provided as rounded edges.

16. The implant needle of claim 1 in which the hollow needle main body has an opening extending in a longitudinal direction of the implant needle.

17. The implant needle of claim 16 in which the opening is a slot opening.

18. The implant needle of claim 17 in which the slot extends the entire length of the hollow needle main body.

19. The implant needle of claim 18 in which the slot is formed symmetric with respect to the longitudinal axis of the hollow needle main body.

\* \* \* \* \*